United States Patent
Nakano et al.

(10) Patent No.: US 6,524,535 B1
(45) Date of Patent: Feb. 25, 2003

(54) ADSORPTION, DECOMPOSITION DEODORIZATION ELEMENT

(75) Inventors: Yoshiki Nakano, Kanagawa (JP); Eiki Iida, Kanagawa (JP); Ryouji Aikawa, Kanagawa (JP)

(73) Assignee: Nikki-Universal Co., Ltd., Tokyo (JP)

( * ) Notice: Subject to any disclaimer, the term of this patent is extended or adjusted under 35 U.S.C. 154(b) by 0 days.

(21) Appl. No.: 09/486,286

(22) PCT Filed: Aug. 21, 1998

(86) PCT No.: PCT/JP98/03704

§ 371 (c)(1),
(2), (4) Date: May 18, 2000

(87) PCT Pub. No.: WO99/10018

PCT Pub. Date: Mar. 4, 1999

(30) Foreign Application Priority Data

Aug. 25, 1997 (JP) .............................................. 9-243360

(51) Int. Cl.[7] .................................................. A62B 7/08
(52) U.S. Cl. ........................ 422/122; 422/120; 422/125
(58) Field of Search ............................... 422/4, 5, 120, 422/121, 125, 122

(56) References Cited

U.S. PATENT DOCUMENTS 5,334,347 A * 8/1994 Hollander .................... 422/24
5,388,177 A * 2/1995 Ono et al. .................. 392/386

FOREIGN PATENT DOCUMENTS

| JP | 1-189320 A | 7/1989 |
| JP | 2-46852 A | 6/1990 |
| JP | 3-143529 A | 6/1991 |
| JP | 4-188586 A | 7/1992 |
| JP | 5-21137 A | 1/1993 |
| JP | 5-101873 A | 4/1993 |
| JP | 8-150323 A | 6/1996 |

\* cited by examiner

Primary Examiner—Krisanne Thornton
(74) Attorney, Agent, or Firm—Fish & Richardson P.C.

(57) ABSTRACT

An adsorptive decomposition deodorizing element comprising of a heating unit having an electrical heating unit inserted between laminated mica plates and a deodorizing unit located on the peripheral surface of said heating unit which can be heated very quickly, gives little offensive odor even in the step of regeneration by heating, and has a light weight and an excellent processability.

20 Claims, 7 Drawing Sheets

---

—○— EXAMPLE 1
ADSORPTIVE DECOMPOSITION DEODORIZING ELEMENT A1/
10mg/cm²

—□— EXAMPLE 5
ADSORPTIVE DECOMPOSITION DEODORIZING ELEMENT A2/
1.5mg/cm²

—△— EXAMPLE 6
ADSORPTIVE DECOMPOSITION DEODORIZING ELEMENT A3/
20mg/cm²

ADSORPTION, DECOMPOSITION DEODORIZATION ELEMENT

TECHNICAL FIELD

This invention relates to an adsorptive decomposition deodorizing element which adsorbs and eliminates offensive odors and toxic gases (hereinafter referred to as "odor components") at ambient temperature, achieves high electrical energy efficiency in the step of electrical heating, requires only an extremely short rise time to attain a predetermined temperature, can quickly desorb the odor components having been adsorbed in the adsorbent so as to restore the adsorbability of the adsorbent and, at the same time, quickly oxidize and decompose the odor components having been adsorbed in the adsorbent and desorbed therefrom.

BACKGROUND ART

To adsorb and eliminate odor components, there have been employed adsorbents such as active carbon, zeolite, silica gel and alumina. Also, it has been a practice to catalytically decompose odor components by using oxidative decomposition catalysts. Moreover, there have been developed devices for adsorbing, decomposing and eliminating odor components by combining these techniques.

For example, JP (Kokai) Hei 4-79963 has disclosed a deodorizing device for eliminating odor components in the atmosphere with the use of an adsorbent, characterized by providing with a heating means for heating the adsorbent, a catalyst capable of making the odor components, which have been liberated from the adsorbent upon heating, odorless and harmless, and another heating means for heating the catalyst.

Further, there have been developed various heating means for desorbing the adsorbed odor components and then oxidatively decomposing the same.

For example, JP (Kokai) Hei 2-194816 has disclosed a technique for heating a deodorizing unit by using a heater which is located in the vicinity of the deodorizing unit and controlled intermittently. In the detailed description in the specification of this patent, a defroster for a refrigerator is cited as a particular example of the heater. In this case, however, the deodorizing unit cannot always achieve a satisfactory rate of temperature rise upon heating, since the heater is located in the vicinity thereof.

JP (Kokai) Hei 2-213080 has disclosed a heating device characterized by having a catalyst-coating layer on the surface thereof. In the detailed description of this patent, it is stated that examples of the heating unit useable in the heating device include coiled metal wires such as nichrome wires and kanthal wires, those in which these metal wires are enclosed in tubes made of metals, quartz or ceramics such as cordierite, mullite, alumina, zirconia, magnesia or calcia, and ceramic heaters in which electrically resistant units are enclosed in ceramics.

Further, JP (Kokai) Hei 7-246317 has disclosed an deodorizing element comprising a metallic fin providing a heater, an enamel layer formed on the surface of the fin by application and burning, and a catalyst layer formed on the enamel layer. However, such a heater or element has a large heat capacity per se and thus cannot always achieve a satisfactory heating speed. Thus, the deodorizing element has a tendency to be heated unevenly in many cases, and it is difficult to heat it uniformly.

Furthermore, JP (Kokai) Hei 7-302678 has disclosed a heating unit obtained by forming a crystallized glass layer on the surface of an electrically resistant heater and further forming a catalyst layer thereon. In the detailed description of the specification of this patent, it is stated that the crystallized glass is excellent in electrical insulating properties and adhesiveness and, therefore, it is possible to construct a small-sized heating unit. It is also stated that since the catalyst layer is located in contact with the crystallized glass layer, the catalyst layer is heated to the activation temperature of the catalyst within a short time, which makes it possible to provide a small-sized heating unit with a short rise time for eliminating and deodorizing harmful gases.

As described above, there have been developed deodorizing and cleaning techniques which comprise eliminating odor components by using adsorbents at ambient temperature, electrically heating the adsorbents either regularly or irregularly to desorb the odor components having been adsorbed therein so as to restore the adsorbability of the adsorbents and, at the same time, regenerating the catalytic activity of oxidation catalysts carried on the adsorbents by heating to the activation temperature, thus oxidatively decomposing the odor components having been adsorbed in the adsorbents and desorbed therefrom, and then repeating the above procedure to thereby eliminate the odor components for a long period of time without replacing the deodorizing unit. Also, there have been developed various means for heating deodorants consisting of adsorbents and catalysts.

Namely, a deodorant is heated so that the odor components having been adsorbed therein are efficiently desorbed and eliminated therefrom. At the same time, an oxidation catalyst carried on the adsorbent is also heated to thereby evoke its catalytic activity and thus the odor components having been adsorbed in the adsorbent and desorbed therefrom are efficiently oxidized, thus preventing the evolution of the offensive odor from the desorbed odor components. To achieve these objects, it is necessary to quickly heat up the adsorbent and the oxidation catalyst carried thereon respectively to the desorption temperature of the odor components and the reaction temperature at which the oxidation activity can be sufficiently evoked. However, the conventional heating means can frequently fail to achieve a sufficient heating speed or uniform heating. Moreover, many conventional heating means require much electrical energy and have some difficulty in processing, which restricts the patterns of the deodorizing elements. Accordingly, it has been urgently required to develop a heating means by which the above-mentioned problems can be solved, the rise time to attain a reaction temperature and the cooling period following the completion of the reaction can be shortened, uniform heating can be achieved, the evolution of any offensive odor can be prevented in the step of the regeneration thereof by heating, the heat volume of the deodorizing element can be reduced so as to save on energy consumption, and the regeneration can be performed by safe heating ever in a limited space without exerting any undesirable effect on the surroundings, thus achieving a high degree of design freedom. The present invention aims at providing an adsorptive decomposition deodorizing element which can be heated very quickly, gives little offensive odor in the step of regeneration thereof by heating, and is of light weight and exhibits excellent processability.

DISCLOSURE OF INVENTION

The present inventors have conducted extensive studies to develop an adsorptive decomposition deodorizing element which ensures an accelerated heating speed and improved uniform heating and is of light weight and exhibits excellent processability, thus being flexible and applicable for various designs. As a result, they have paid attention to mica which is of light weight, has excellent mechanical properties (electrical insulating properties, heat conductivity, mechanical strength, thermal coefficient of expansion, etc.) and a high heat resistance and can be easily processed into various complicated shapes owing to its excellent cutting and punching processability. Thus, they have developed an adsorptive decomposition deodorizing element consisting of an electrical heating unit inserted between laminated mica plates and a deodorizing unit located on the peripheral surface thereof by which odor components are adsorbed and then oxidatively decomposed by heating. The present invention has been completed based on this finding.

Accordingly, the present invention relates to an adsorptive decomposition deodorizing element comprising a heating unit having an electrical heating unit inserted between laminated mica plates and a deodorizing unit located on the peripheral surface of said heating unit.

One of the parts of the adsorptive decomposition deodorizing element of the present invention is a heating unit having an electrical heating unit inserted between laminated mica plates.

BEST MODE FOR CARRYING OUT THE INVENTION

The mica to be used in the present invention may be one arbitrarily selected from natural mica, synthetic mica, composite materials thereof, etc. without restriction, so long as it has a high flexural strength and a good heat resistance, sustains a high strength and a high insulation resistance even at high temperatures and shows neither fuming nor evolution of any offensive odor upon heating. Natural mica, which falls within the group of layered silicate minerals, involves white mica $[K_2Al_4(Al_2Si_6O_{20})(OH)_4]$, gold mica $[K_2Mg_6(Al_2Si_6O_{20})(OH,F)_4]$, black mica $[K_2(Mg,Fe)_6(Al_2Si_6O_{20})(OH)_4]$, etc. Synthetic mica is exemplified by synthetic fluorinated mica prepared by replacing hydroxyl ion with fluorine ion. Mica is classified into hard mica produced in India $[KAl_2(Al,Si)_4O_{10})(OH,F)_2]$ and soft mica produced in Madagascar $[KMg_3(Al,Si)_4O_{10})(OH,F)_2]$ and the soft mica is preferable since it has a high strength and good insulation properties at a high temperature of 600° C.

Laminated mica plates can be prepared by adhering mica sheets to each other by using an adhesive, compressing the same by heating and then completely hardening the adhesive at an elevated temperature. Although laminated mica plates can be processed into various forms, they are usually molded into sheets so as to enlarge the effective area of the adsorptive decomposition deodorizing element, thus enhancing adsorbability.

The electrical heating unit may be made of any electrically heating material capable of emitting heat when an electrical current is passed therethrough. For example, a metal wire consisting of a commonly employed electrical heating unit made of an alloy (for example, iron-chromium, nickel-chromium, iron-nickel-chromium, tungsten or kanthal) and electrical terminals provided at both ends thereof is regularly folded or an electrically heated foil is molded into a desired shape to give an electrical heating unit.

It is preferable that the electrical heating unit is not too wide but, rather, is uniformly distributed, as far as possible, over the heating parts of the heating unit. When the electrical heating unit area is too large as compared with the whole area of the heating parts, or the electrical heating unit is too wide and thus the laminated mica plates are exposed only in a small area, the adhesiveness of the laminated mica plates to each other is lowered. As a result, the mica paper plates are liable to peel off, thus causing a deterioration in the strength of the heating unit. The width of the electrical heating unit preferably ranges from 1 to 2 mm. It is also preferable from the viewpoint of adhesiveness that the electrical heating unit is not a round wire but in the form of a foil, a ribbon or a thin film. It is preferable that the electrical heating unit is uniformly distributed onto the whole heating parts at intervals of from 1 to 5 mm.

It is also one of the preferable embodiments of the present invention to regulate the resistance by forming on the surface of the laminated mica plate a thick film of a composition obtained by adding a ceramic powder to a powder of a high-melting metal (tungsten, molybdenum, tantalum, platinum, rhodium, etc.) by the conventional printing method and providing the ends thereof with electrical terminals.

It is preferable to construct the heating unit by uniformly enclosing the above-mentioned electrical heating unit between the above-mentioned laminated mica plates and then effecting adhesion with a silicone adhesive followed by compression by heating.

When mica plates are not integrally fused together but merely layered on each other, the electrical heating unit may adhere to the mica plates insufficiently. In such a case, there frequently arises a difference in temperature between the mica plates on either side. When a electrical current is turned on, moreover, the temperature distribution becomes uneven in each of the mica plates which have not been integrally fused together. Thus, the heating unit is liable to be deformed due to the difference in thermal expansion, which often makes the heating unit crooked in the step of electrical heating.

It is, therefore, most desirable to integrally fuse the heating unit having the electrical heating unit therein. The thickness of the heating unit preferably ranges from 0.6 to 3.0 mm, still preferably from 1.0 to 2.0 mm.

Another part of the adsorptive decomposition deodorizing element of the present invention is the deodorizing unit located on the peripheral surface of the heating unit. This deodorizing unit is composed of an adsorbent and an oxidation catalyst.

The adsorbent may be an arbitrary one without restriction, so long as it is a heat resistant material capable of adsorbing odor components. For example, use may be made of natural zeolites (active alumina, silica alumina, chabasite, mordenite, erionite, faujasite, clinoptilolite, etc.) and synthetic zeolites (Zeolite A, Zeolite X, Zeolite Y, Zeolite L, Zeolite Omega, ZSM-5, etc.) either alone or as a mixture thereof. Preferable examples of the zeolite include crystalline silica having a silica/alumina ratio of at least 12 and crystalline silica almost free from alumina, i.e., silicalite. Silicalite is the most desirable one, since its ability to adsorb odor components is scarcely affected by the moisture in the atmosphere.

The oxidation catalyst may be an arbitrary one, so long as it can oxidize and decompose the odor components having been desorbed. Preferable examples of the oxidation catalyst include elements of the platinum group such as platinum, palladium, osmium, iridium and rhodium; elements of the iron group such as iron, cobalt and nickel; elements of the group I such as copper and silver; elements of the group VII such as manganese; and rare earth metals such as cerium and lanthanum. Either one of these metals or an appropriate combination thereof may be used as the catalytic component. The catalytic component can be carried on in the form of the metal element, its oxide or a composite of the same in a conventional manner. It may be appropriately replaced by the zeolite.

The deodorizing unit is carried on the heating unit at a ratio of from 1 to 30 mg/cm$^2$, preferably from 5 to 25 mg/cm$^2$. When the amount of the deodorizing unit is too small, no effective deodorizing effect can be established. On the other hand, use of the deodorizing unit in an excessively large amount exhibits undesirable effects on the rate of rise in temperature during heating and, furthermore, deteriorates the carriage strength, thus causing peeling.

EXAMPLES

To further illustrate the present invention in greater detail, and not by way of limitation, the following Examples, Comparative Examples and Test Examples will be given.

Example 1

Figures 6, 7:
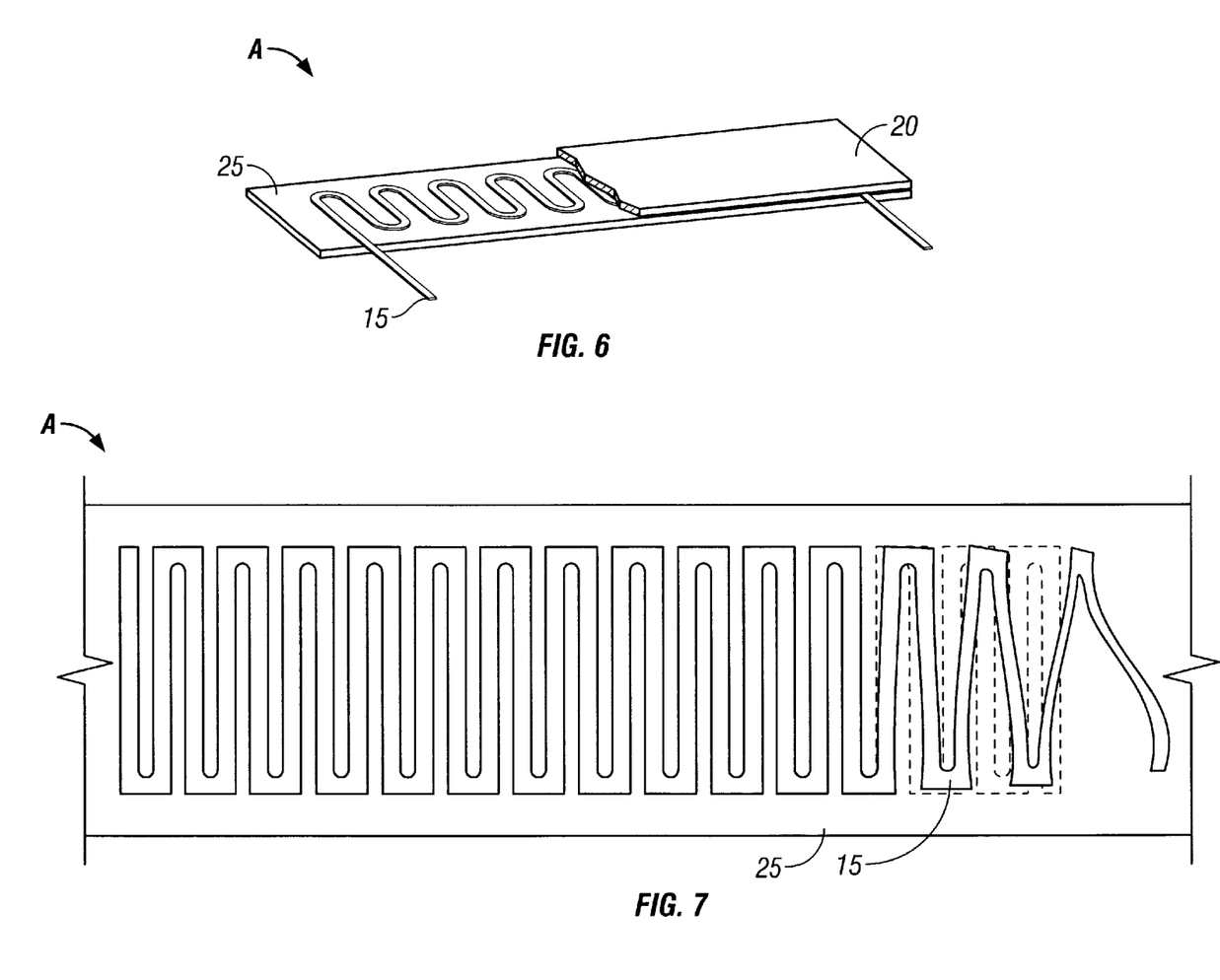
FIG. 6 is a perspective view of the heating unit of Example 1.
FIG. 7 is a photograph of an electrical heating unit and laminated mica paper of Example 1.
Figure 8:
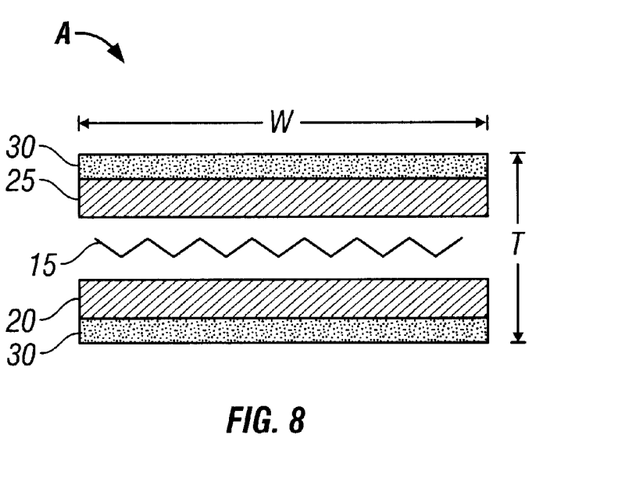
FIG. 8 is a cross-sectional side view of an adsorptive decomposition deodorizing element including the heating unit of Example 1.

Referring to FIGS. 6 and 7, a heating unit A includes an iron-chromium foil electrical heating unit 15 positioned between an upper soft mica paper sheet 20 and a lower soft mica paper sheet 25. The upper soft mica paper sheet 20 and the lower soft mica paper sheet 25 each have an outer surface, which together comprise the peripheral surface of the heating unit. Referring also to FIG. 8, the finished heating unit A includes the deodorizing unit 30, described above, located on the peripheral surface of the heating unit. The finished heating unit A has a thickness, T, and a width, W. The iron-chromium foil is 3,400 mm in full length, 0.053 mm in thickness and 1.2 mm in width and was molded into a zigzag configuration with folding intervals of 1.7 mm (width=30 mm, length of each folded part=300 mm) to thereby construct an electrical heating unit having an electrical resistance of 67 Ω and an electrical capacity of 150 W/100 V.

Separately, soft mica paper sheets for electrical heating (Z523TM, manufactured by Nippon Mica Seisakusho) of 0.5 mm in thickness were cut into pieces of 40 mm in width and 400 mm in length. Between these laminated mica plates, the above-mentioned electrical heating unit was inserted in such a manner as to place both ends of the electrical heating unit outside the mica paper plates by using a binder prepared by dissolving a solid silicone resin in an organic solvent. Then the obtained composite material was molded by heating to a final temperature of 350° C. under elevated pressure to thereby give a heating unit A which was 0.9 mm in thickness, 40 mm in width and 400 mm in length and weighed 32 g. The heating unit A thus obtained had an effective heating length of 330 mm, an effective surface area of 264 cm$^2$, an effective heating part weight of 26.4 g and a weight per effective unit surface area of 0.100 g/cm$^2$.

83 parts by weight of high-silica zeolite (S-115TM, manufactured by UOP, including 3.6% by weight of loss on heating), 4 parts by weight of cupric acetate monohydrate of reagent grade (manufactured by Wako Pure Chemical Industries, Ltd., containing 40.5% by weight of CuO), 5 parts by weight of ceria (CeO$_2$, manufactured by JGC Corporation) and 10 parts by weight of an active alumina powder (TNTM, manufactured by Nikki Universal, including 3% by weight of loss on heating) were mixed together in a ball mill for 4 hours to give a dry powder. The resultant powder was spread in a vat made of SUS and burned in an airflow type muffle furnace at a temperature of 300° C. for 30 minutes and then at a temperature of 350° C. for 30 minutes to give a burned powder.

To a solution prepared by mixing 36 parts by weight of deionized water with 2 parts by weight of an acidic solution of dinitrodiamine platinum nitric acid (Hakkin P Salt™, manufactured by Tanaka Kikinzoku Kogyo, containing 5% by weight of Pt) were added 16 parts by weight of the burned powder prepared above and 6 parts by weight of a silica powder (Feselex-XTM, manufactured by Tatsumori). After stirring for 30 minutes, 40 parts by weight of alumina sol (Alumina Sol 200TM, containing 10% by weight of alumina) was added thereto and mixed by stirring. After mixing and grinding in a wet ball mill for additional 4 hours, a deodorizing coating M was obtained.

The surface of the above-mentioned heating unit A was wiped with acetone and then cleaned by burning in an airflow type muffle furnace at a temperature of 400° C. for 30 minutes. The cleaned heating unit surface was heated with a dryer. Next, the deodorizing coating M was quickly sprayed onto the effective heating parts (40 mm in width and 330 mm in length at the center of the heating unit) in both faces of the heating unit so that the whole heating unit was almost uniformly moistened but no coating dropped therefrom, followed by drying with a hair dryer. This procedure was repeated until the application dose of the deodorizing coating onto the heating unit attained 10 mg/cm$^2$ on a dry basis. The heating unit was dried in a dryer at a temperature of 150° C. for 30 minutes and then burned in an air flow type muffle furnace at a temperature of 400° C. for 1 hour. Thus, an adsorptive decomposition deodorizing element A1 having 2.64 g/element, on a dry basis, of the deodorizing coating M applied thereon was prepared. The adsorptive decomposition deodorizing element A1 thus obtained had a weight per effective unit surface area of 0.110 g/cm². Table 1 shows the rise time to attain a predeterminded temperature and electrical power of this element, while Table 2 shows the temperature distribution therein.

Example 2

A heating unit B, which was 0.6 mm in thickness, 40 mm in width and 400 mm in length and weighed 21 g, was prepared by the same procedures as those described in Example 1 but using soft mica paper sheets for electrical heating of 0.3 mm in thickness as a substitute for those 0.5 mm in thickness. The heating unit B thus obtained had an effective heating length of 330 mm, an effective surface area of 264 cm², an effective heating part weight of 17.35 g and a weight per effective unit surface area of 0.066 g/cm².

Similar to Example 1, the deodorizing coating M was then quickly applied onto the effective heating parts of the heating unit B at a rate of 10 mg/cm² on a dry basis to thereby give an adsorptive decomposition deodorizing element B having 2.64 g/element, on a dry basis, of the deodorizing coating M applied thereon was prepared. The adsorptive decomposition deodorizing element B thus obtained had a weight per effective unit surface area of 0.076 g/cm². Table 1 shows the rise time to attain a predetermined temperature and electrical power of this element, while Table 2 shows the temperature distribution therein.

Example 3

Figure 9:
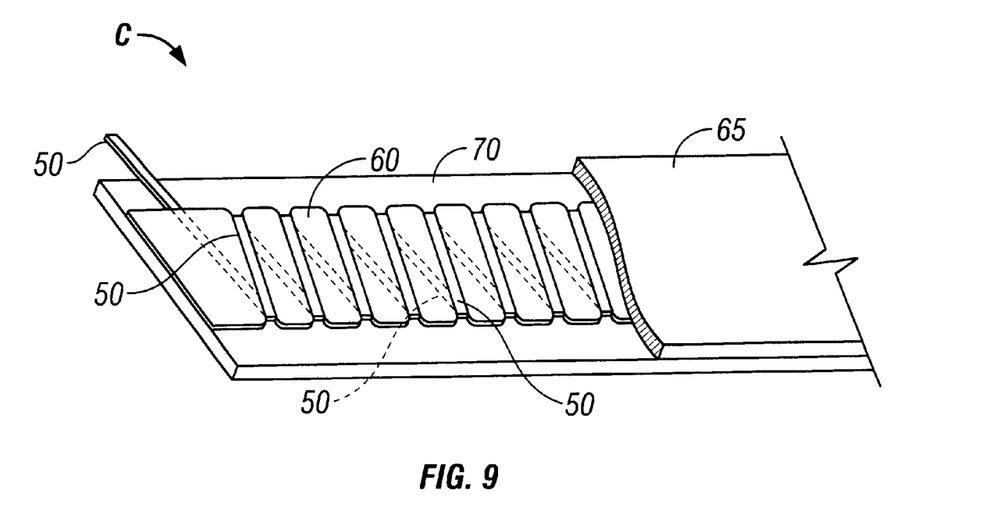
FIG. 9 is a perspective view of the heating unit of Example 3.

Referring to FIG. 9, a heating unit C includes an iron-chromium heating wire 50 positioned within grooves or cuts 55 of an intermediate soft mica paper sheet 60 and wound around the sheet 60 in a spiral configuration. The intermediate soft mica paper sheet 60 and spirally wound wire 50 are positioned between an upper soft mica paper sheet 65 and a lower soft mica paper sheet 70. The upper soft mica paper sheet 65 and the lower soft mica paper sheet 70 each have an outer surface, which together comprise the peripheral surface of the heating unit C.

Similar to Example 1, soft mica paper sheets for electrical heating (manufactured by Nippon Mica Seisakusho) of 0.4 mm in thickness were cut into pieces of 40 mm in width and 400 mm in length. In one of these mica plates, cuts (1 mm in width, 5 mm in depth) were made in both ends in the width direction at intervals of 10 mm at the center in the length direction over 300 mm in such a manner as to alternately arrange the cuts in the both ends in the width direction, thus forming an intermediate plate. Next, an iron-chromium heating wire, which was 1,950 mm in full-length and 0.2 mm in diameter and had an electrical resistance of 67 Ω and an electric capacity of 150 W/100 V, was spirally wound around the intermediate plate while putting the wire into each cut and taking the both ends of the wire outside the mica plate. The intermediate plate having the heating wire wound therearound was inserted between two other mica plates. Then these three mica plates were fixed together by wiring at intervals of 50 to 100 mm to thereby give a heating unit C which was 1.6 mm in thickness, 40 mm in width and 400 mm in length, weighed 46 g and had an electric capacity of 150 W/100 V. The heating unit C thus obtained had an effective heating length of 330 mm, an effective surface area of 264 cm², an effective heating part weight of 37.95 g and a weight per effective unit surface area of 0.144 g/cm².

Similar to Example 1, the deodorizing coating M was then quickly applied onto the effective heating parts of the heating unit C at a rate of 10 mg/cm² on a dry basis to thereby give an adsorptive decomposition deodorizing element C having 2.64 g/element, on a dry basis, of the deodorizing coating M applied thereon was prepared. The adsorptiive decomposition deodorizing element C thus obtained had a weight per effective unit surface area of 0.154 g/cm². Table 1 shows the rise time to attain a predeterminded temperature and electrical power of this element, while Table 2 shows the temperature distribution therein.

Example 4

The procedure of Example 3 was repeated but making cuts of 2 mm in width and 5 mm in depth at intervals of 6 mm in the intermediate plate and using an iron-chromium wire of 0.05 in thickness and 1.2 mm in width. Thus a heating unit D which was 1.3 mm in thickness, 40 mm in width and 400 mm in length, weighed 45 g and had an electric capacity of 150 W/100 V was prepared. The heating unit D thus obtained had an effective heating length of 330 mm, an effective surface area of 264 cm², an effective heating part weight of 37.15 g and a weight per effective unit surface area of 0.141 g/cm².

Similar to Example 1, the deodorizing coating M was then quickly applied onto the effective heating parts of the heating unit D at a rate of 10 mg/cm² on a dry basis to thereby give an adsorptive decomposition deodorizing element D having 2.64 g/element, on a dry basis, of the deodorizing coating M applied thereon was prepared. The adsorptive decomposition deodorizing element D thus obtained had a weight per effective unit surface area of 0.151 g/cm². Table 1 shows the rise time to attain a predeterminded temperature and electrical power of this element, while Table 2 shows the temperature distribution therein.

Comparative Example 1

A stainless sheath heater having an electric capacity of 250 W/100V, a diameter of 6 mm and a length of 500 mm was inserted between radiating plates made of aluminized steel (1 mm in thickness, 30 mm in width and 400 mm in length) followed by pressing. Thus a sheath heater X provided with a fin which weighed 265 g and had an external surface area of the radiating plates of 240 cm² was obtained. The effective heating parts of the obtained sheath heater X weighed 256 g and its weight per effective unit surface area was 1.067 g/cm². Namely, this sheath heater X was heavier by one order of magnitude than those of the present invention as described in the above Examples. As a matter of course, this heater of Comparative Example 1 had a larger heat capacity.

The surface of the radiating plates of the fin heater X was wiped with acetone, dried at a temperature of 150°0 C. and then cleaned by burning at a temperature of 400° C. for 30 minutes. Next, an inorganic adhesive (Sumiseram-S208CTM, manufactured by Asahi Kagaku Kogyo) was uniformly applied with a brush onto the radiating plate surface thus cleaned to give an application dose of about 5 mg/cm² after burning. Then it was air-dried at room temperature for 1 hour, dried at a temperature of 150° C. for 30 minutes and then heated at a temperature of 300° C. for 1 hour. Next, the deodorizing coating M prepared in Example 1 was applied onto the surface of the radiating plates thus coated with the inorganic adhesive, as done in Example 1 at a application dose of 10 mg/cm² on a dry basis. Thus, an adsorptive decomposition deodorizing element X having 2.4 g/element, on a dry basis, of the deodorizing coating M applied thereon was prepared. The adsorptive decomposition deodorizing element X thus obtained had a weight per effective unit surface area of 1.082 g/cm². Table 1 shows the rise time to attain a predetermined temperature and electrical power of this element.

Comparative Example 2

A mica strip heater (MH Standard Model Space Heater™, manufactured by Sakaguchi Dennetsu; 6 mm in thickness, 37 mm in width and 480 mm in length) having an electric capacity of 375 W/100 V, which had been constructed by winding a nickel-chromium wire ribbon for electrical heating around an intermediate mica plate, inserting the intermediate plate between insulating mica plates and further coating it with a metal plate followed by pressing, was referred to as a strip heater Y. This strip heater Y had an effective heating part of 375 mm in length and 460 g in weight. Its effective surface area was 323 cm2 and the weight per effective unit surface area thereof was 1.424 g/cm². Namely, this strip heater Y was heavier by one order of magnitude than those of the present invention as described in the above Examples. As a matter of course, this heater of Comparative Example 2 had a larger heat capacity.

The procedure of Comparative Example 1 was repeated but using this strip heater Y as a substitute for the fin heater X. Thus, an adsorptive decomposition deodorizing element Y having 5 mg/cm², after burning, of the inorganic adhesive and 10 mg/cm², after drying, of the deodorizing coating M applied thereon was prepared. The adsorptive decomposition deodorizing element Y thus obtained had 3.23 g/element, on a dry basis, of the deodorizing coating M applied thereon and its weight per effective unit surface area was 1.439 g/cm². Table 1 shows the rise time to attain a predeterminded temperature and electrical power of this element.

Comparative Example 3

A heater provided with a stainless steel sheath (Strip Heater™, manufactured by Vulcan Electric; 37 mm in width, 387 mm in length and 8 mm in thickness) weighing 376 g and having an electric capacity of 450 W/100 V was referred to as a strip heater Z. This strip heater Z had an effective heating part of 290 mm in length and 321 g in weight. Its effective surface area was 261 cm² and the weight per effective unit surface area thereof was 1.230 g/cm². Namely, this strip heater Z was heavier by one order of magnitude than those of the present invention as described in the above Examples. As a matter of course, this heater of Comparative Example 3 had a larger heat capacity.

The procedure of Comparative Example 1 was repeated but using this strip heater Z as a substitute for the fin heater X. Thus, an adsorptive decomposition deodorizing element Z having 5 mg/cm², after burning, of the inorganic adhesive and 10 mg/cm², after drying, of the deodorizing coating M applied thereon was prepared. The adsorptive decomposition deodorizing element Z thus obtained had 2.61 g/element, on a dry basis, of the deodorizing coating M applied thereon and its weight per effective unit surface area was 1.245 g/cm². Table 1 shows the rise time to attain a predeterminded temperature and electrical power of this element.

Example 5

The procedure of Example 1 was repeated but applying the deodorizing coating M in an application dose of 1.5 mg/cm² on a dry basis to thereby give an adsorptiive decomposition deodorizing element A2 having 0.40 g/element of the deodorizing coating M applied thereon. The adsorptive decomposition deodorizing element A2 thus obtained had a weight per effective unit surface area of 0.102 g/cm².

Example 6

The procedure of Example 1 was repeated but applying the deodorizing coating M in an application dose of 20 mg/cm² on a dry basis to thereby give an adsorptive decomposition deodorizing element A3 having 5.28 g/element of the deodorizing coating M applied thereon. The adsorptiive decomposition deodorizing element A3 thus obtained had a weight per effective unit surface area of 0.120 g/cm².

Test Example 1

Each adsorptive decomposition deodorizing element was placed on a thermally and electrically insulated support located in a room at ambient temperature under moderate humidity. The electrical resistant terminals projected from the adsorptive decomposition deodorizing element were connected to each other via an ammeter, a volt meter and a current regulator so that an electrical current could pass therethrough. The surface temperature of the adsorptive decomposition deodorizing element was measured with an infrared radiation thermometer (Model IT2, manufactured by KEYENCE) and the voltage required for maintaining the surface temperature at 250° C. was detected by controlling the electrical current regulator.

Figure 1:
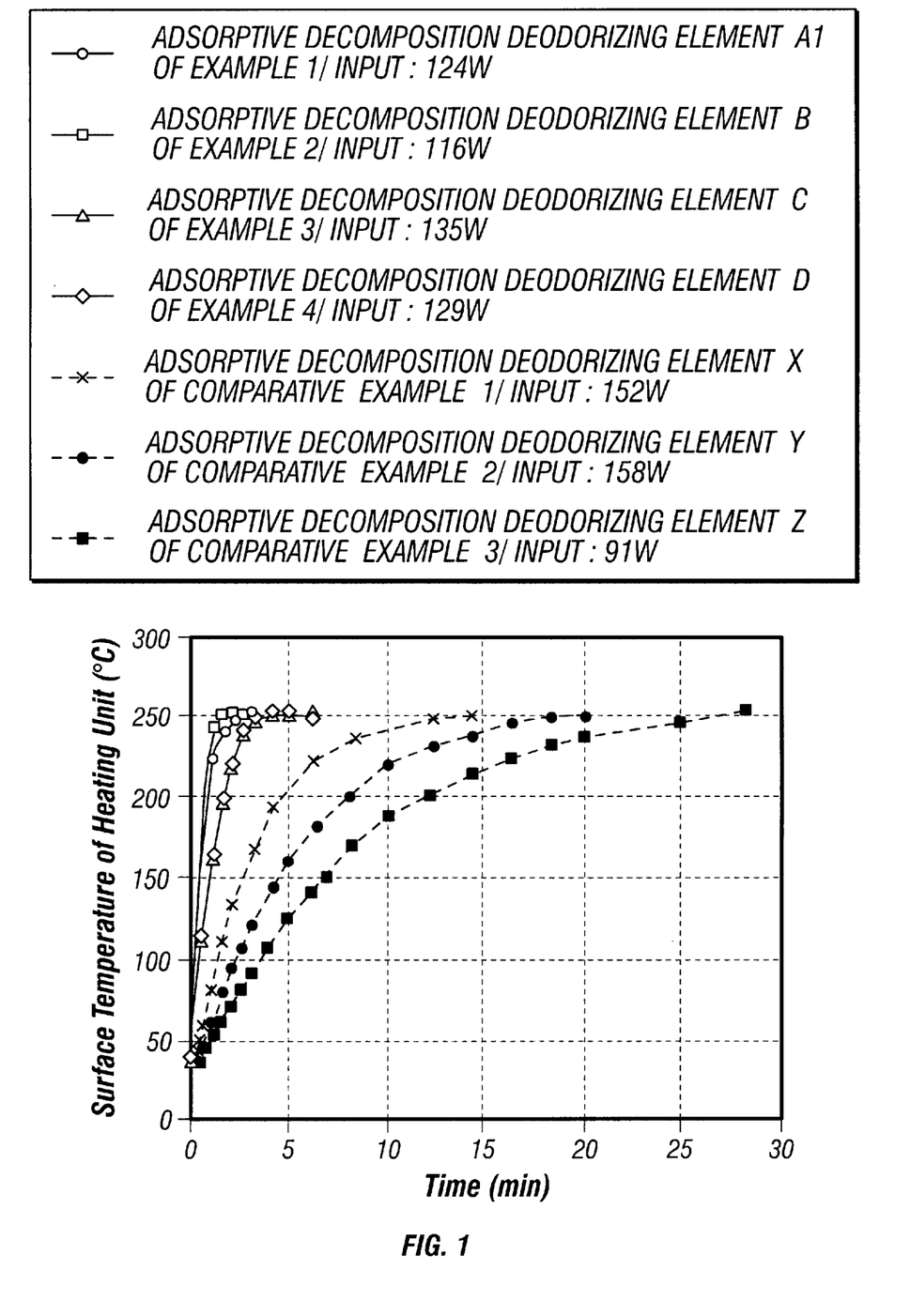
FIG. 1 is a graph which shows the rate of rise in the surface temperature of the adsorptive decomposition deodorizing elements in Examples and Comparative Examples when an electric current was turned thereon.
Figure 2:
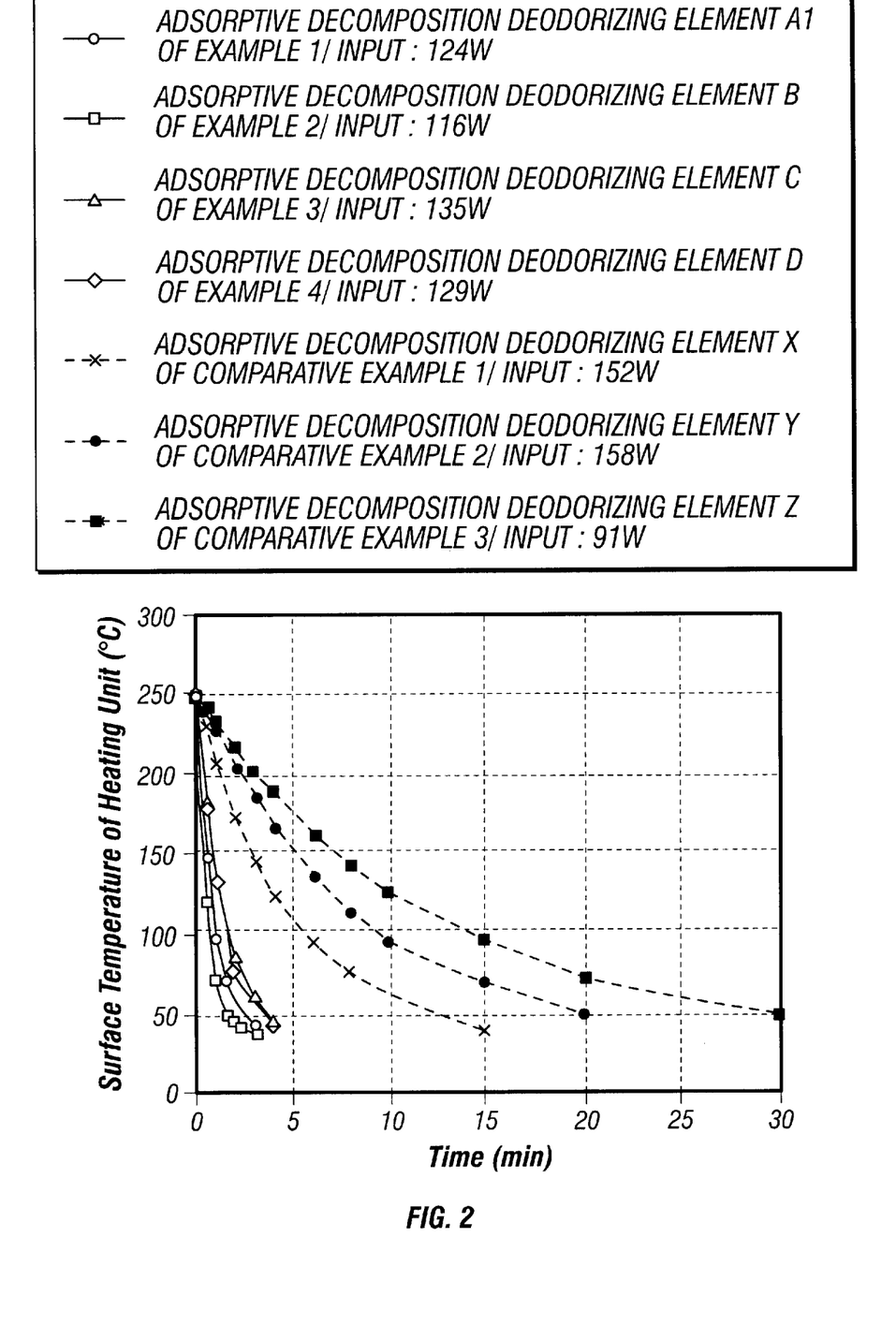
FIG. 2 is a graph which shows the rate of fall in the surface temperature of the adsorptive decomposition deodorizing elements in Examples and Comparative Examples when these elements were heated up to a surface temperature of 250° C. and then cooled down by being allowed to stand.

Then, the voltage thus detected was applied onto the adsorptive decomposition deodorizing element at ambient temperature and the rise time required for attaining a surface temperature of the adsorptive decomposition deodorizing element of 250° C. was measured. Also, the relationship between the time passed after turning off the electric current and the surface temperature of the adsorptive decomposition deodorizing element was examined. FIGS. 1 and 2 show the results.

Table 1 summarizes the voltage (V) required for maintaining a surface temperature of the adsorptive decomposition deodorizing elements at 250° C., the time (min) required for attaining the surface temperature of 250° C. and the electrical capacity (W) and electrical power (W.h) of the adsorptive decomposition deodorizing elements.

Table 2 shows the results of the measurement of a surface temperature distribution of the adsorptive decomposition deodorizing elements when the surface temperature reached the steady state at a temperature of 250° C.

TABLE 1

| Adsorptive Decomposition Deodorizing Element | Voltage (V) | Electric Capacity (W) | Time (min) | Electrical Power (W.h) |
|---|---|---|---|---|
| A1 | 91 | 124 | 3.0 | 6.2 |
| B | 88 | 116 | 1.5 | 2.9 |
| C | 95 | 135 | 4.5 | 10.1 |
| D | 93 | 129 | 4.5 | 9.7 |
| X | 78 | 152 | 14.0 | 35.5 |
| Y | 65 | 158 | 20.0 | 52.7 |
| Z | 45 | 91 | 27.0 | 41.0 |

As Table 1 clearly shows, the adsorptive decomposition deodorizing elements A1, B, C and D of the present invention prepared in Examples 1, 2, 3 and 4 attained the predetermined temperature of 250° C. within a short period of time, almost proportionally to the weight per efficient unit surface area, with less electricity consumption, compared with the fin sheath heater type adsorptive decomposition deodorizing element of Comparative Example 1 and the slip heater type adsorptive decomposition deodorizing elements of Comparative Examples 2 and 3. That is to say, it has been confirmed that the adsorptive decomposition deodorizing element of the present invention can be heated quickly while using smaller electrical energy, which indicates that the adsorptive decomposition deodorizing element of the present invention is highly advantageous from an economical viewpoint.

TABLE 2

| Adsorptive Decomposition Deodorizing Element | Interval of Electrically Heating wire (mm) | Surface temperature of Adsorptive Decomposition Deorization Element | |
|---|---|---|---|
| | | Just above Wire (° C.) | Intermediate of Wire (° C.) |
| A1 | 1.7 | 250 | 249 |
| B | 1.7 | 250 | 249 |
| C | 10.0 | 250 | 227 |
| D | 4.8 | 250 | 246 |

Table 2 clearly shows that as the intervals of the electrical resistance wire were enlarged, the surface temperature of the intermediate part of the electrical resistance wire became lower than the surface temperature just above the electrical resistance wire, thus showing an uneven temperature distribution. It has been thus proved that the surface temperature of the adsorptive decomposition deodorizing element of the present invention becomes uneven when the intervals of the electrical resistance wire exceeds 5 mm.

As FIG. 1 shows, the adsorptive decomposition deodorizing elements A1, B, C and D of Examples 1, 2, 3 and 4 of the present invention showed very high rate of temperature rise after turning on the electrical current. Namely, the surface temperature of the heater attained 250° C. within 90 to 240 seconds. Among all, the adsorptive decomposition deodorizing elements A1 and B of Examples 1 and 2 having mica plates and the electrical heating unit integrated together showed high heat conductivity and little heat loss, thus achieving a high rate of rise in surface temperature. In particular, the adsorptive decomposition deodorizing element B of Example 2, in which thinner mica plates were employed, showed an extremely high rate of rise in temperature. In contrast, the adsorptive decomposition deodorizing elements C and D of Examples 3 and 4, wherein mica plates having the electrical heating unit wound therearound were layered on each other and fixed by wiring, were somewhat poor in uniform adhesiveness between the heating wire and the mica plates. In these elements, therefore, the weight per effective unit surface area was increased and the rate of temperature rise was somewhat lowered due to air entering into the space between the mica plates. In the adsorptive decomposition deodorizing elements C and D which showed low rate of temperature rise among the adsorptive decomposition deodorizing elements of the present invention, a rise time of 4.5 minutes was required to attain the surface temperature of 250° C. after the electrical current was turned on at ambient temperature. In contrast, the fin sheath heater-type adsorptive decomposition deodorizing element X of Comparative Example 1 and the strip heater type adsorptive decomposition deodorizing elements Y and Z of Comparative Examples 2 and 3 each showed a rate of rise in the surface temperature 3 or more times lower than those of the adsorptive decomposition deodorizing elements C and D. That is to say, even the fin sheath heater type adsorptive decomposition deodorizing element X of Comparative Example 1, which showed the highest rate of rise in among the adsorptive decomposition deodorizing elements of Comparative Examples, showed a rise time of 14 minutes. It has been thus proved that the adsorptive decomposition deodorizing element of the present invention has heat characteristics with a good rising.

As FIG. 2 shows, the adsorptive decomposition deodorizing elements of the present invention are superior in the rate of fall in the temperature too. Namely, the adsorptive decomposition deodorizing element of the present invention consisting of a heating unit having an electrical heating unit inserted between laminated mica plates and a deodorizing unit located on the peripheral surface of said heating unit adsorbs odor components and thus eliminates the same at ambient temperature. When an electrical current is turned thereon, it can efficiently utilize the electrical energy and the deodorizing unit is heated with a good rising. Thus, the odor components having been adsorbed by the adsorbent are desorbed therefrom and the adsorbability of the adsorbent can be thus regenerated. At the same time, the desorbed odor components are oxidatively decomposed efficiently. When the electrical current is turned off, the temperature of the adsorptive decomposition deodorizing element can be lowered so that the odor components can be adsorbed thereby again and eliminated. It has been thus proved that the adsorptive decomposition deodorizing element of the present invention is excellent in the deodorizing performance and repeated usability.

Test Example 2

Figure 3:
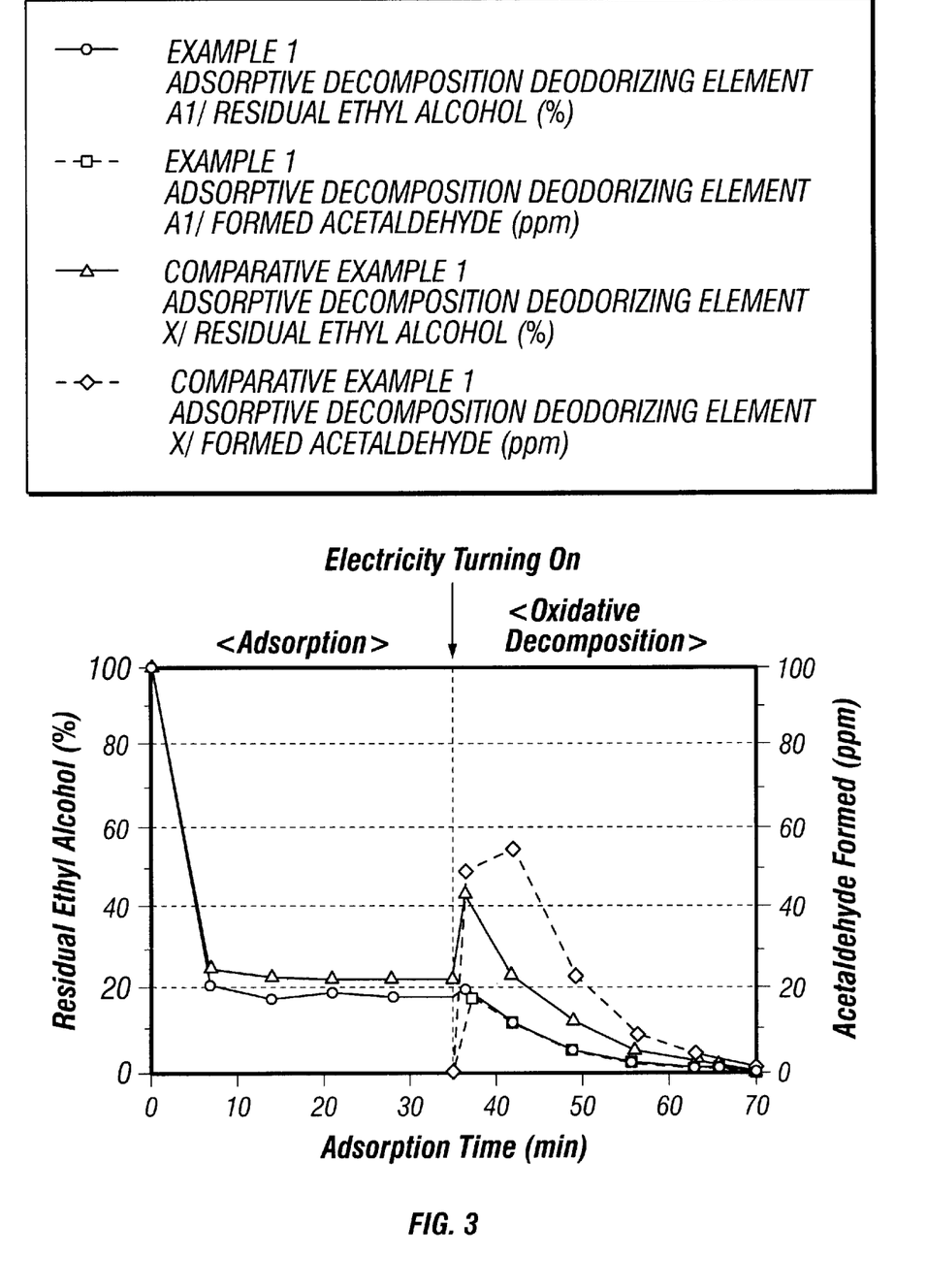
FIG. 3 shows the adsorbability of the adsorptive decomposition deodorizing elements of Example 1 and Comparative Example 1 when ethyl alcohol was adsorbed thereby and the ability of these elements to desorb and decompose the thus adsorbed ethyl alcohol upon electrical heating.

An adsorptive decomposition deodorizing element sample, which had been electrically heated up to a temperature of 250° C. so as to restore its adsorbability, was placed in a closed glass reactor (30 liters) at ambient temperature under a relative humidity regulated to 90%. Then 15.6 microliters of ethyl alcohol was injected thereinto while stirring with a fan provided in the container. After adjusting the ethyl alcohol concentration in the container to 200 ppm, the adsorptive decomposition deodorizing element was allowed to adsorb the ethyl alcohol. After 35 minutes, the stirring of the fan was ceased and the voltage required for maintaining the surface temperature of the adsorptive decomposition deodorizing element at 250° C., which had been determined in the above Test Example 1, was applied onto the adsorptive decomposition deodorizing element for 35 minutes. Thus the ethyl alcohol having been adsorbed and stored in the adsorptive decomposition deodorizing element was desorbed therefrom and, at the same time, oxidatively decomposed. Changes in the ethyl alcohol and acetaldehyde concentrations in the container were monitored by using FID gas chromatography. FIG. 3 shows the change in the acetaldehyde concentration with the passage of time and the amount (%) of the residual ethyl alcohol based on the starting concentration.

Figure 4:
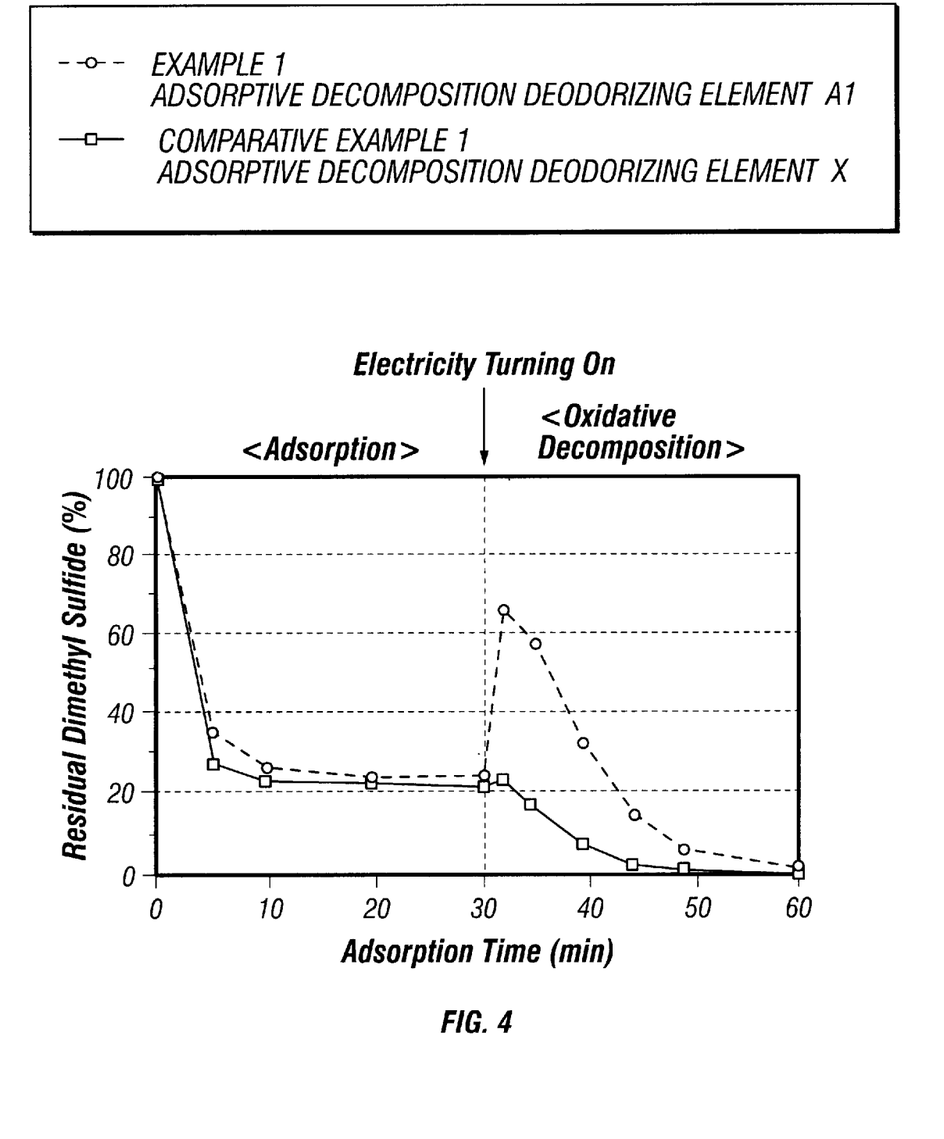
FIG. 4 shows the adsorbability of the adsorptive decomposition deodorizing elements of Example 1 and Comparative Example 1 when dimethyl sulfide was adsorbed therein and the ability of these elements to desorb and decompose the thus adsorbed dimethyl sulfide upon electrical heating.
Figure 5:
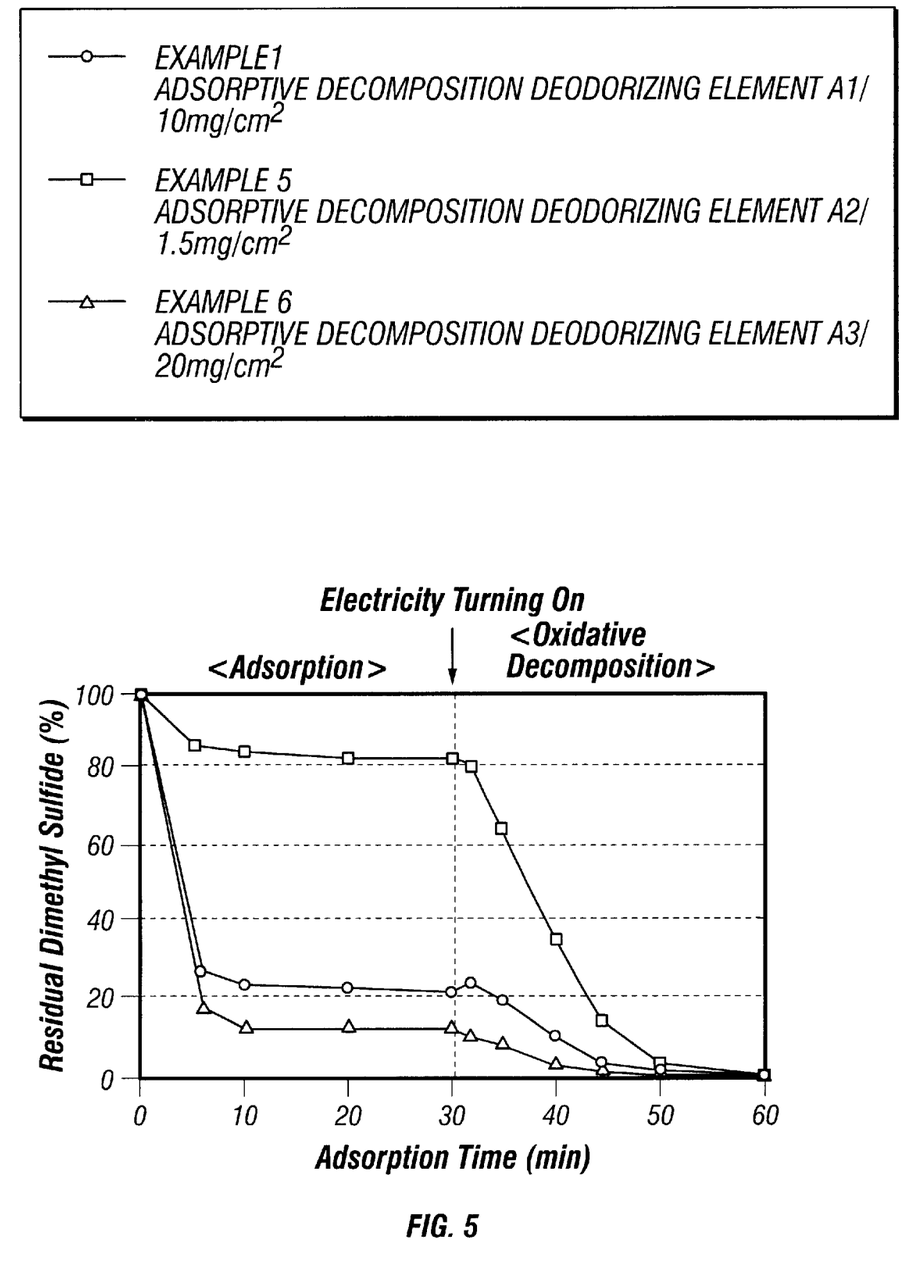
FIG. 5 shows the difference in the abilities to absorb, desorb and oxidatively decompose dimethyl sulfide depending on the application dose of deodorizing coating.

The above test procedure was repeated but injecting 19.8 microliters of dimethyl sulfide and the adsorption time and the oxidative decomposition time were each adjusted to 30 minutes. FIGS. 4 and 5 show the amount (%) of the residual dimethyl sulfide based on the starting concentration.

As FIG. 3 clearly shows, in the adsorptive decomposition deodorizing element A1 of the present invention of Example 1, the ethyl alcohol concentration showed no increase after turning on the electric current and the amount of the residual ethyl alcohol was lowered due to the oxidative decomposition. In this case, little acetaldehyde, i.e., an intermediate in the oxidative decomposition reaction of ethyl alcohol, was formed. In the adsorptive decomposition deodorizing element X of Comparative Example 1, on the other hand, the ethyl alcohol having been desorbed from the element could not be well oxidatively decomposed for a while after turning on the electrical current, due to the low rate of temperature rise. In this case, therefore, the ethyl alcohol concentration showed an increase for about 10 minutes after turning on the electrical current and acetaldehyde, i.e., the reaction intermediate was increased for about 15 minutes after heating.

As FIG. 4 clearly shows, in the case of dimethyl sulfide, the adsorptive decomposition deodorizing element X of Comparative Example 1 showed an obvious increase in the dimethyl sulfide concentration for a while after heating since the oxidative decomposition reaction could proceed only insufficiently due to the low rate of temperature rise. In contrast thereto, the adsorptive decomposition deodorizing element A1 of Example 1 of the present invention showed a quick rise to attain the temperature necessary for the oxidative decomposition. Namely, this element was heated quickly and the dimethyl sulfide desorbed therefrom was efficiently decomposed, thus showing no increase in the dimethyl sulfide concentration. When an electrical current is turned on the adsorptive decomposition deodorizing element of the present invention, it can efficiently utilize the electrical energy and the deodorizing unit is heated with a good rising. Thus, the odor components having been adsorbed by the adsorbent are desorbed and the adsorbability can be regenerated. At the same time, the desorbed odor components can be oxidatively decomposed efficiently. Accordingly, neither undecomposed odor components due to the low rate of temperature rise nor newly formed odor components, i.e., intermediates caused by the insufficient reaction are liberated from the element of the present invention. It has been thus proved that the adsorptive decomposition deodorizing element of the present invention is excellent in its effect, scarcely showing the evolution of any offensive odor in the step of the regeneration by heating.

FIG. 5 shows the adsorption and oxidative decomposition of dimethyl sulfide by using three adsorptive decomposition deodorizing elements of the present invention differing from each other in the application dose of the deodorizing coating. As FIG. 5 indicates, the adsorbability increases in proportion to the application dose. However, the application dose of the deodorizing coating per unit surface area is restricted to 30 mg/cm$^2$ or less in order to sustain the adhesion strength of the deodorizing coating and the rate of surface temperature rise in the adsorptive decomposition deodorizing element.

Test Example 3

The adsorptive decomposition deodorizing elements A1, A2 and A3 of the present invention obtained in Examples 1, 5 and 6 were treated for 250 cycles with each cycle consisting of heating up to a temperature of 300° C. by turning on an electrical current for 5 minutes, then turning off the electrical current and air-cooling the elements with a fan for 5 minutes. As a result, any of the adsorptive decomposition deodorizing elements showed neither peeling nor deterioration in the adsorbability or oxidative decomposition performance.

Industrial Applicability (1) The adsorptive decomposition deodorizing element of the present invention can be used for cleaning air by adsorbing and eliminating various odor components contained therein for household and business purposes.

(2) Because of having a light weight and a compact and slim shape, the adsorptive decomposition deodorizing element of the present invention can be easily loaded on devices. Moreover, it has a small heat capacity and, therefore, exerts little undesirable thermal effect on the surroundings, which highly elevates the degree of freedom in designing.

(3) The adsorptive decomposition deodorizing element of the present invention has a light weight and a small heat capacity and carries the deodorizing unit directly located on the peripheral surface of laminated mica plates constituting the heating unit. Thus, it shows a very high heat conductivity and the deodorizing unit can be quickly heated electrically. Owing to these characteristics, excessive electrical energy is not used and operating efficiency can be attained.

(4) In the adsorptive decomposition deodorizing element of the present invention, the temperature can be quickly elevated to the reaction temperature of the catalyst. Thus, the odor components liberated from the heated adsorbent can be quickly and efficiently oxidized and decomposed, thus scarcely causing the evolution of any offensive odor in the step of the regeneration by heating.

(5) Since an even temperature distribution is achieved in the adsorptive decomposition deodorizing element of the present invention during heating, little undecomposed odor components are liberated therefrom and thus any offensive odor is scarcely evolved in the step of the regeneration by heating.

(6) After turning off the electric current, the adsorptive decomposition deodorizing element of the present invention is quickly cooled and thus the adsorbability of the adsorbent can be rapidly restored.

(7) The adsorptive decomposition deodorizing element of the present invention can be regenerated by heating and thus repeatedly employed.

We claim:

1. An adsorptive decomposition deodorizing element comprising a heating unit having an electrical heating unit inserted between laminated mica plates and a deodorizing unit located on the laminated mica plates.

2. The adsorptive decomposition deodorizing element as claimed in claim 1, wherein said deodorizing unit comprises an adsorbent capable of adsorbing odor components at ambient temperature, and a catalyst capable of oxidatively decomposing said odor components thus adsorbed thereby and odor components desorbed from said adsorbent by electrical heating.

3. The adsorptive decomposition deodorizing element as claimed in claim 1, wherein the laminated mica plates comprise mica sheets adhered to each other by an adhesive.

4. The adsorptive decomposition deodorizing element as claimed in claim 1, wherein the electrical heating unit comprises one of a foil, a ribbon, or a thin film.

5. The adsorptive decomposition deodorizing element as claimed in claim 1, wherein the electrical heating unit comprises a film formed on a surface of one of the laminated mica plates.

6. The adsorptive decomposition deodorizing element as claimed in claim 1, wherein the electrical heating unit is adhered to the laminated mica plates with an adhesive.

7. The adsorptive decomposition deodorizing element as claimed in claim 1, wherein a thickness of the heating unit is between approximately 0.6 mm and 3.0 mm.

8. The adsorptive decomposition deodorizing element as claimed in claim 1, wherein a thickness of the heating unit is between approximately 1.0 mm and 2.0 mm.

9. The adsorptive decomposition deodorizing element as claimed in claim 1, wherein the adsorbent comprises zeolite.

10. The adsorptive decomposition deodorizing element as claimed in claim 9, wherein the zeolite comprises silicalite.

11. The adsorptive decomposition deodorizing element as claimed in claim 1, wherein the catalyst comprises one or more of platinum, palladium, osmium, iridium, and rhodium.

12. The adsorptive decomposition deodorizing element as claimed in claim 1, wherein the catalyst comprises one or more of iron, cobalt, and nickel.

13. The adsorptive decomposition deodorizing element as claimed in claim 1, wherein the catalyst comprises one or more of copper, silver, and manganese.

14. The adsorptive decomposition deodorizing element as claimed in claim 1, wherein the catalyst comprises one or more of cerium and lanthanum.

15. The adsorptive decomposition deodorizing element as claimed in claim 1, wherein the deodorizing unit is present on the peripheral surface at a ratio of between 1 and 30 mg/cm$^2$.

16. The adsorptive decomposition deodorizing element as claimed in claim 1, wherein the deodorizing unit is present on the laminated mica plates at a ratio of between 5 and 25 mg/cm$^2$.

17. The adsorptive decomposition deodorizing element as claimed in claim 1, further comprising an intermediate laminated mica plate positioned between the upper laminated mica plate and the lower laminated mica plate and around which the electrical heating unit is wound.

18. The adsorptive decomposition deodorizing element as claimed in claim 17, wherein the intermediate laminated mica plate comprises one or more cuts along a width direction and the electrical heating unit passes through the cuts.

19. An adsorptive decomposition deodorizing element comprising:

a heating unit having an electrical heating unit inserted between laminated mica plates; and a deodorizing unit located on the laminated mica plates, wherein said deodorizing unit comprises an adsorbent capable of adsorbing odor components at ambient temperature and a catalyst capable of oxidatively decomposing said odor components thus adsorbed thereby and odor components desorbed from said adsorbent by electrical heating, the laminated mica plates comprise mica sheets adhered to each other by an adhesive, and the electrical heating unit comprises an iron-chromium foil.

20. The adsorptive decomposition deodorizing element as claimed in claim 19, wherein the laminated mica plates are integrally fused together.

* * * * *